United States Patent [19]
Haas et al.

[11] Patent Number: 5,554,761
[45] Date of Patent: Sep. 10, 1996

[54] HERBICIDAL SULPHONYLAMINO-CARBONYLTRIAZOLINONES HAVING TWO SUBSTITUENTS BONDED VIA OXYGEN

[75] Inventors: Wilhelm Haas, Pulheim; Klaus-Helmut Müller, Düsseldorf; Klaus König, Odenthal; Hans-Joachim Santel, Leverkusen; Klaus Lürssen; Robert R. Schmidt, both of Bergisch Gladbach, all of Germany

[73] Assignee: Bayer Aktiengesellschaft, Leverkusen, Germany

[21] Appl. No.: 547,698

[22] Filed: Oct. 19, 1995

Related U.S. Application Data

[62] Division of Ser. No. 174,495, Dec. 28, 1993, Pat. No. 5,488,028, which is a division of Ser. No. 945,194, Sep. 15, 1992, Pat. No. 5,300,480, which is a continuation-in-part of Ser. No. 31,426, Mar. 15, 1993, Pat. No. 5,405,970, which is a continuation-in-part of Ser. No. 816,365, Dec. 30, 1991, Pat. No. 5,241,074, which is a division of Ser. No. 692,439, Apr. 29, 1991, Pat. No. 5,094,683, which is a division of Ser. No. 556,052, Jul. 20, 1990, Pat. No. 5,057,144, which is a continuation-in-part of Ser. No. 337,775, Apr. 13, 1989, abandoned.

[30] Foreign Application Priority Data

May 9, 1988 [DE] Germany ............... 38 15 769.9
Oct. 12, 1989 [DE] Germany ............... 39 34 081.3
Sep. 25, 1991 [DE] Germany ............... 41 31 842.0

[51] Int. Cl.$^6$ ............................................. C07D 249/12
[52] U.S. Cl. ............................................. 548/263.6
[58] Field of Search ............................................. 548/263.6

[56] References Cited

U.S. PATENT DOCUMENTS

5,021,080  6/1991  Muller et al. .
5,057,144  10/1991 Daum et al. .
5,085,684  2/1992  Muller et al. .
5,094,683  2/1992  Daum et al. .
5,300,480  4/1994  Hans et al. .

FOREIGN PATENT DOCUMENTS

477646  3/1992  European Pat. Off. .

Primary Examiner—Patricia L. Morris
Attorney, Agent, or Firm—Sprung Horn Kramer & Woods

[57] ABSTRACT

Herbicidal sulphonylaminocarbonyltriazolinones having two substituents bonded via oxygen, of the formula $$R^3-SO_2-NH-CO-N\underset{N=\!\!=\!\!\underset{O-R^2}{\overset{}{\diagdown}}}{\overset{\overset{\displaystyle O}{\|}}{\diagup\!\!\diagdown}} N-O-R^1 \qquad (I)$$

in which $R^1$ represents hydrogen or an optionally substituted radical from the series comprising alkyl, alkenyl, alkinyl, cycloalkyl, cycloalkenyl and aralkyl, $R^2$ represents an optionally substituted radical from the series comprising alkyl, alkenyl, alkinyl, cycloalkyl, cycloalkenyl and aralkyl, and $R^3$ represents an optionally substituted radical from the series comprising alkyl, aralkyl, aryl and heteroaryl, and their salts.

6 Claims, No Drawings

HERBICIDAL SULPHONYLAMINOCARBONYLTRIAZOLINONES HAVING TWO SUBSTITUENTS BONDED VIA OXYGEN

This application is a divisional, of application Ser. No. 08/174,495, filed on Dec. 28, 1993 now U.S. Pat. No. 5,488,028, which is a division of Ser. No. 07/945,194, filed on Sep. 15, 1992 now U.S. Pat. No. 5,300,480, which is a continuation-in-part of application Ser. No. 08/031,426 filed on Mar. 15, 1993, now U.S. Pat. No. 5,405,970, which is a continuation-in-part of application Ser. No. 07/816,365, filed Dec. 30, 1991 now U.S. Pat. No. 5,241,074, which is a division of application Ser. No. 07/692,439 filed Apr. 29, 1991, now U.S. Pat. 5,094,683, which is a division of application Ser. No. 07/556,052, filed Jul. 20, 1990, now U.S. Pat. No. 5,057,144, which is a continuation-in-part of application Ser. No. 07/337,775, filed Apr. 13, 1989, now abandoned entitled HERBICIDAL SULPHONYLAMINOCARBONYLTRIAZOLINONES HAVING TWO SUBSTITUENTS BONDED VIA OXYGEN.

The invention relates to new sulphonylaminocarbonyltriazolinones having two substituents bonded via oxygen to a plurality of processes and new intermediates for their preparation, and to their use as herbicides.

It has been disclosed that certain substituted sulphonylaminocarbonyltriazolinones such as, for example, 2-(2-chloro-phenylsulphonylaminocarbonyl)-4,5-dimethyl-2,4-dihydro-3H,1,2,4-triazol-3-one, have herbicidal properties (cf. EP-A 341,489; cf. also EP-A 422,469, EP-A 425,948 and EP-A 431,291). However, the action of these compounds is not satisfactory in all respects.

Sulphonylaminocarbonyltriazolinones having one substituent which is bonded via oxygen (in the 5-position) are the subject of a previous, but non-prior-published Patent Application (cf. German Patent Specification 4,110,795.0 [LeA 28318] dated 04.04.1991).

There have now been found the new sulphonylaminocarbonyltriazolinones having two substituents bonded via oxygen of the general formula (I)

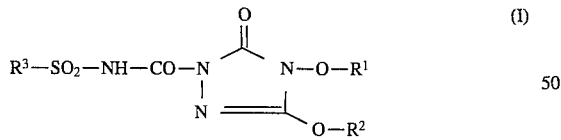

in which
R¹ represents hydrogen or an optionally substituted radical from the series comprising alkyl, alkenyl, alkinyl, cycloalkyl, cycloalkenyl and aralkyl,
R² represents an optionally substituted radical from the series comprising alkyl, alkenyl, alkinyl, cycloalkyl, cycloalkenyl and aralkyl, and
R³ represents an optionally substituted radical from the series comprising alkyl, aralkyl, aryl and heteroaryl,
and salts of compounds of the formula (I).

The new sulphonylaminocarbonyltriazolinones having two substituents bonded via oxygen of the general formula (I) are obtained when (a) triazolinones of the general formula (II)

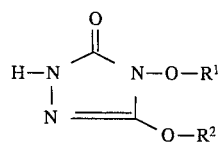

in which
R¹ and R² have the abovementioned meanings, are reacted with, sulphonyl isocyanates of the general formula (III)

in which
R³ has the abovementioned meaning,
if appropriate in the presence of a diluent, or when (b) triazolinone derivatives of the general formula (IV)

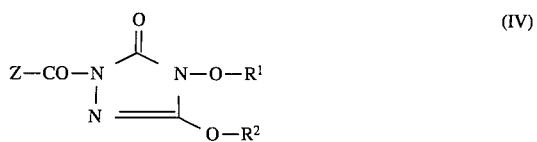

in which
R¹ and R² have the abovementioned meanings and
Z represents halogen, alkoxy, aralkoxy or aryloxy,
are reacted with sulphonamides of the general formula (V)

in which
R³ has the abovementioned meaning,
if appropriate in the presence of an acid acceptor and if appropriate in the presence of a diluent, or when (c) triazolinones of the general formula (II)

in which
R¹ and R² have the abovementioned meanings,
are reacted with sulphonamide derivatives of the general formula (VI)

in which
R³ has the abovementioned meaning and
Z represents halogen, alkoxy, aralkoxy or aryloxy,
if appropriate in the presence of an acid acceptor and if appropriate in the presence of a diluent, and, if appropriate, salts are formed with the compounds of the formula (I) prepared by process (a), (b) or (c), using customary methods.

The new sulphonylaminocarbonyltriazolinones having two substituents bonded via oxygen of the formula (I) and their salts are distinguished by a powerful herbicidal activity.

Surprisingly, the new compounds of the formula (I) show a considerably better herbicidal action than the compound 2-(2-chlorophenylsulphonylaminocarbonyl)-4,5-dimethyl2,4-dihydro-3H-1,2,4-triazol-3-one, which is known and which has a similar structure.

The invention preferably relates to compounds of the formula (I) in which $R^1$ represents hydrogen, or represents $C_1$–$C_6$-alkyl which is optionally substituted by fluorine, chlorine, bromine, cyano, $C_1$–$C_4$-alkoxy, $C_1$–$C_4$-alkylcarbonyl or $C_1$–$C_4$-alkoxy-carbonyl, or represents $C_3$–$C_6$-alkenyl or $C_3$–$C_6$-alkinyl, each of which is optionally substituted by fluorine, chlorine and/or bromine, or represents $C_3$–$C_7$-cycloalkyl or $C_4$–$C_7$-cycloalkenyl, each of which is optionally substituted by fluorine, chlorine, bromine and/or $C_1$–$C_4$-alkyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, $R^2$ represents $C_1$–$C_6$-alkyl which is optionally substituted by fluorine, chlorine, bromine, cyano, $C_3$–$C_6$-cycloalkyl, $C_1$–$C_4$-alkoxy or $C_1$–$C_4$-alkoxy-carbonyl, or represents $C_3$–$C_6$-alkenyl or $C_3$–$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents cyclohexenyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxycarbonyl, and $R^3$ represents the group

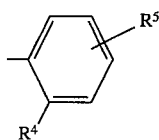

where
$R^4$ and $R^5$ are identical or different and represent hydrogen, fluorine, chlorine, bromine, iodine, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylamino-carbonyl, di-($C_1$–$C_4$-alkyl)amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl), or represents $C_2$–$C_6$-alkenyl (which is optionally substituted by fluorine, chlorine, bromine, cyano, $C_1$–$C_4$-alkoxycarbonyl, carboxyl or phenyl), or represents $C_2$–$C_6$-alkinyl (which is optionally substituted by fluorine, chlorine, bromine, cyano, $C_1$–$C_4$-alkoxy-carbonyl, carboxyl or phenyl), or represents $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or represents $C_1$–$C_4$-alkylthio (which is optionally substituted by fluorine, chlorine, bromine, cyano, carboxyl, $C_1$–$C_4$-alkoxycarbonyl, $C_1$–$C_4$-alkylthio, $C_1$–$C_4$-alkylsulphinyl or $C_1$–$C_4$-alkylsulphonyl), or represents $C_3$–$C_6$-alkenyloxy (which is optionally substituted by fluorine, chlorine, bromine, cyano or $C_1$–$C_4$-alkoxy-carbonyl), or represents $C_2$–$C_6$-alkenylthio (which is optionally substituted by fluorine, chlorine, bromine, cyano, nitro, $C_1$–$C_3$-alkylthio or $C_1$–$C_4$-alkoxycarbonyl), $C_3$–$C_6$-alkinyloxy, $C_3$–$C_6$-alkinylthio, or the radical —S(O)$_p$—$R^6$ where
represents the numbers 1 or 2 and $R^6$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino, phenyl, or the radical —NHOR$^7$, where
$R^7$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl), or represents $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxy-carbonyl), or represents benzhydryl, or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), $R^4$ and/or $R^5$ furthermore represent phenyl or phenoxy, or represent $C_1$–$C_4$-alkylcarbonylamino, $C_1$–$C_4$-alkoxy-carbonylamino, $C_1$–$C_4$-alkylamino-carbonyl-amino, di-($C_1$–$C_4$-alkyl)-amino-carbonylamino, or represent the radical —CO—$R^8$, where
$R^8$ represents $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (each of which is optionally substituted by fluorine and/or chlorine), $R^4$ and $R^5$ furthermore represent trimethylsilyl, thiazolinyl, $C_1$–$C_4$-alkylsulphonyloxy, di-($C_1$–$C_4$-alkyl)-aminosulphonylamino or represents the radical —CH=N—$R^9$ where
represents $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, or represents benzyl which is optionally substituted by fluorine or chlorine, or represents $C_3$–$C_6$-alkenyl or $C_3$–$C_6$-alkinyl, each of which is optionally substituted by fluorine or chlorine, or represents phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, or represents $C_1$–$C_6$-alkoxy, $C_3$–$C_6$-alkenoxy, $C_3$–$C_6$-alkinoxy or benzyloxy, each of which is optionally substituted by fluorine and/or chlorine, or represents amino, $C_1$–$C_4$-alkylamino, di-($C_1$–$C_4$-alkyl)-amino, phenylamino, $C_1$–$C_4$-alkyl-carbonyl-amino, $C_1$–$C_4$-alkoxy-carbonylamino, $C_1$–$C_4$-alkyl-sulphonylamino, or represents phenylsulphonylamino which is optionally substituted by fluorine, chlorine, bromine or methyl, furthermore $R^3$ represents the radical

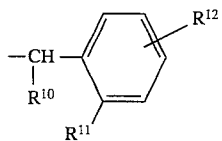

where
$R^{10}$ represents hydrogen or $C_1$–$C_4$-alkyl,
$R^{11}$ and $R^{12}$ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), carboxyl, $C_1$–$C_4$-alkoxy-carbonyl, dimethylaminocarbonyl, $C_1$–$C_4$-alkylsulphonyl or di-($C_1$–$C_4$-alkyl)-aminosulphonyl;

furthermore $R^3$ represents the radical

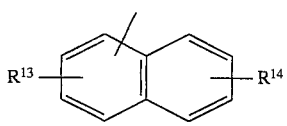

where
$R^{13}$ and $R^{14}$ are identical or different and represent hydrogen, fluorine, chlorine, bromine, nitro, cyano, $C_1$–$C_4$-alkyl (which is optionally substituted by fluorine and/or chlorine) or $C_1$–$C_4$-alkoxy (which is optionally substituted by fluorine and/or chlorine);

furthermore $R^3$ represents the radical

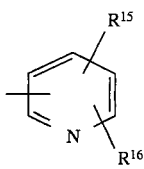

where
$R^{15}$ and $R^{16}$ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), or represent $C_1$–$C_4$-alkylthio, $C_1$–$C_4$-alkylsulphinyl or $C_1$–$C_4$-alkylsulphonyl (which are optionally substituted by fluorine and/or chlorine), or represent aminosulphonyl, mono-($C_1$–$C_4$-alkyl)-aminosulphonyl, or represent di-($C_1$–$C_4$-alkyl)-aminosulphonyl or $C_1$–$C_4$-alkoxycarbonyl or dimethylaminocarbonyl;

furthermore $R^3$ represents the radical

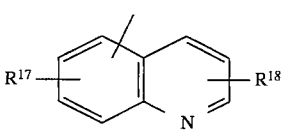

where
$R^{17}$ and $R^{18}$ are identical or different and represent hydrogen, fluorine, chlorine, bromine, $C_1$–$C_4$-alkyl (which is optionally substituted by fluorine and/or bromine), $C_1$–$C_4$-alkoxy (which is optionally substituted by fluorine and/or chlorine), or represent $C_1$–$C_4$-alkylthio, $C_1$–$C_4$-alkylsulphinyl or $C_1$–$C_4$-alkylsulphonyl (which are optionally substituted by fluorine and/or chlorine), or represent di-($C_1$–$C_4$alkyl)-amino-sulphonyl;

furthermore $R^3$ represents the radical

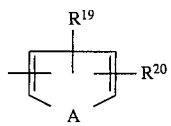

where
$R^{19}$ and $R^{20}$ are identical or different and represent hydrogen, fluorine, chlorine, bromine, cyano, nitro, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio, $C_1$–$C_4$-alkylsulphinyl or $C_1$–$C_4$-alkylsulphonyl (which is optionally substituted by fluorine and/or chlorine), di-($C_1$–$C_4$-alkyl)-aminosulphonyl, $C_1$–$C_4$-alkoxy-carbonyl or dimethyl-aminocarbonyl, and A represents oxygen, sulphur or the group N—$Z^1$, where
$Z^1$ represents hydrogen, $C_1$–$C_4$-alkyl (which is optionally substituted by fluorine, chlorine, bromine or cyano), $C_3$–$C_6$-cycloalkyl, benzyl, phenyl (which is optionally substituted by fluorine, chlorine, bromine or nitro), $C_1$–$C_4$-alkylcarbonyl, $C_1$–$C_4$-alkoxy-carbonyl or di-($C_1$–$C_4$-alkyl)-aminocarbonyl;

furthermore $R^3$ represents the radical

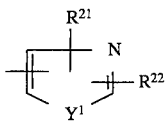

where
$R^{21}$ and $R^{22}$ are identical or different and represent hydrogen, $C_1$–$C_4$-alkyl, halogen, $C_1$–$C_4$-alkoxy-carbonyl, $C_1$–$C_4$-alkoxy or $C_1$–$C_4$-halogenoalkoxy,
$Y^1$ represents sulphur or the group N—$R^{23}$, where
$R^{23}$ represents hydrogen or $C_1$–$C_4$-alkyl;

furthermore $R^3$ represents the radical

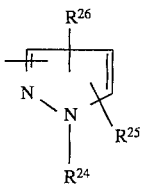

where
$R^{24}$ represents hydrogen, $C_1$–$C_4$-alkyl, benzyl, pyridyl, quinolinyl or phenyl,
$R^{25}$ represents hydrogen, halogen, cyano, nitro, $C_1$–$C_4$-alkyl (which is optionally substituted by fluorine and/or chlorine), $C_1$–$C_4$-alkoxy (which is optionally substituted by fluorine and/or chlorine), dioxolanyl or $C_1$–$C_4$-alkoxy-carbonyl, and $R^{26}$ represents hydrogen, halogen or $C_1$–$C_4$-alkyl; furthermore $R^3$ represents one of the groups mentioned below,

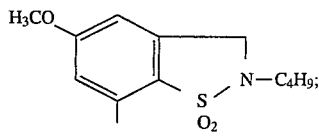

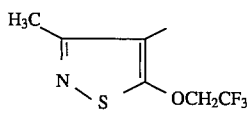

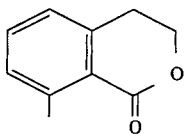

Furthermore, the invention preferably relates to sodium salts, potassium salts, magnesium salts, calcium salts, ammonium salts, $C_1$–$C_4$-alkyl-ammonium salts, di-($C_1$–$C_4$-alkyl)-ammonium salts, tri-($C_1$–$C_4$-alkyl)-ammonium salts, $C_5$- or $C_6$-cycloalkyl-ammonium salts and di-($C_1$–$C_2$-alkyl)-benzyl-ammonium salts of compounds of the formula (I) in which $R^1$, $R^2$ and $R^3$ have the meanings given above as being preferred.

In particular, the invention relates to compounds of the formula (I) in which $R^1$ represents hydrogen, or represents $C_1$–$C_4$-alkyl which is optionally substituted by fluorine, cyano, methoxy or ethoxy, or represents allyl, or represents $C_3$–$C_6$-cycloalkyl, or represents benzyl, $R^2$ represents $C_1$–$C_4$-alkyl which is optionally substituted by fluorine and/or chlorine, methoxy or ethoxy, or represents $C_3$–$C_4$-alkenyl which is optionally substituted by fluorine and/or chlorine, or represents $C_3$–$C_6$-cycloalkyl, or represents benzyl which is optionally substituted by fluorine, chlorine and/or methyl, and $R^3$ represents the group

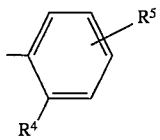

where $R^4$ represents fluorine, chlorine, bromine, methyl, trifluoromethyl, methoxy, trifluoromethoxy, trifluoromethoxy, 2-chloro-ethoxy, 2-methoxyethoxy, $C_1$–$C_3$-alkylthio, $C_1$–$C_3$-alkylsulphinyl, $C_1$–$C_3$-alkylsulphonyl, dimethylaminosulphonyl, diethylaminosulphonyl, N-methoxy-N-methylaminosulphonyl, methoxyaminosulphonyl, phenyl, phenoxy or $C_1$–$C_3$-alkoxy-carbonyl, and $R^5$ represents hydrogen, fluorine, chlorine or bromine; furthermore $R^3$ represents the radical

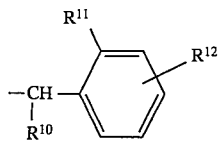

where $R^{10}$ represents hydrogen, $R^{11}$ represents fluorine, chlorine, bromine, methyl, methoxy, difluoromethoxy, trifluoromethoxy, ethoxy, methoxycarbonyl, ethoxycarbonyl, methylsulphonyl or dimethylaminosulphonyl and $R^{12}$ represents hydrogen;

furthermore $R^3$ represents the radical

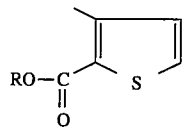

where R represents $C_1$–$C_4$-alkyl, or represents the radical

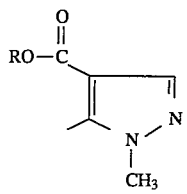

where R represents $C_1$–$C_4$-alkyl.

Examples of the compounds according to the invention are listed in Table 1 below–cf. also the Preparation Examples.

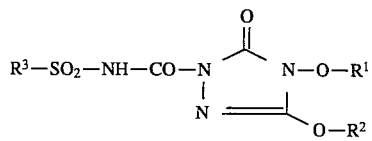

TABLE 1

| | Examples of the compounds of the formula (I) | |
|---|---|---|
| $R^1$ | $R^2$ | $R^3$ |
| △ | CH$_3$ | (F-phenyl) |

TABLE 1-continued
Examples of the compounds of the formula (I)
| R¹ | R² | R³ |
|---|---|---|
|  | CH₃ | 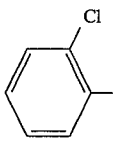 Cl |
| CH₃ | C₂H₅ | 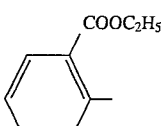 COOC₂H₅ |
| CH₃ | CH₂—CH=CH₂ | 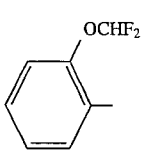 OCHF₂ |
| CH₃ | CH₃ | 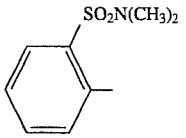 SO₂N(CH₃)₂ |
| CH₃ | CH₃ | 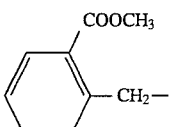 COOCH₃, —CH₂— |
| CH₃ | C₂H₅ | 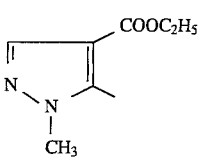 COOC₂H₅, N-N-CH₃ |
| CH₃ | C₂H₅ | 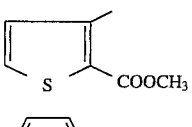 S, COOCH₃ |
| CH₃ | C₂H₅ | 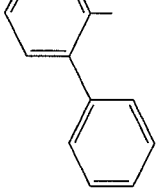 |
| C₂H₅ | C₂H₅ | 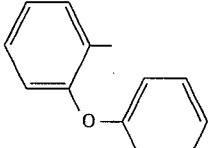 |
| C₂H₅ | C₃H₇ | 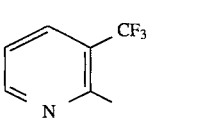 CF₃, N |

TABLE 1-continued

Examples of the compounds of the formula (I)

| R¹ | R² | R³ |
|---|---|---|
| cyclopropyl | $CH_3$ | 2-($OCF_3$)benzyl |
| cyclopropyl | $C_2H_5$ | 2-($OCH_2CH_2Cl$)phenyl |
| cyclopropyl | $CH(CH_3)_2$ | 3-$CON(CH_3)_2$-2-methylpyridinyl |
| $CH_3$ | $CH(CH_3)_2$ | 3-$SO_2NH_2$-2-methylpyridinyl |
| $CH_3$ | $CH_2-CH=CH_2$ | 2-($SCH(CH_3)_2$)phenyl |
| $C_2H_5$ | $CH_3$ | 2-($SO_2CH_3$)phenyl |
| $C_2H_5$ | $CH_3$ | 2-F-phenyl |
| $C_2H_5$ | $C_2H_5$ | 2-$Si(CH_3)_3$-phenyl |
| $C_2H_5$ | $C_3H_7$ | 2-($OCF_3$)benzyl |
| $CH_3$ | $C_2H_5$ | 3-$CON(CH_3)_2$-2-methylpyridinyl |
| benzyl | $CH_3$ | 2-Br-phenyl |

TABLE 1-continued

Examples of the compounds of the formula (I)

| $R^1$ | $R^2$ | $R^3$ |
|---|---|---|
| cyclopropyl | $C_2H_5$ | 2-(OCH$_2$CH$_2$—OCH$_3$)phenyl |
| cyclobutyl | $CH_3$ | 4-bromo-5-methyl-1-methyl-pyrazol-3-yl |
| cyclopentyl | $C_2H_5$ | 2-(SO$_2$N(CH$_3$)$_2$)phenyl |
| 4-H-cyclohexyl | $C_3H_7$-n | 2-OCHF$_2$-phenyl-CH$_2$— |
| $CH_3$ | $C_2H_5$ | 2-COOCH(CH$_3$)$_2$-4-Cl-phenyl |
| $CH_3$ | $CH_3$ | 2-COOC$_2$H$_5$-4-(F$_2$CHO)-phenyl |
| $CH_3$ | $C_2H_5$ | 2-(phenoxy)phenyl |
| $CH_3$ | S—CH$_2$—C≡CH | 2-(thiazol-2-yl)phenyl |
| $CH_3$ | $C_2H_5$ | 2-(O—CH$_2$—CF$_3$)phenyl |

TABLE 1-continued

Examples of the compounds of the formula (I)

| R¹ | R² | R³ |
|---|---|---|
| cyclopropyl | C₂H₅ | 1-phenyl-5-methyl-pyrazole-4-COOCH₃ |
| cyclopropyl | CH₃ | 1-(isoquinolin-1-yl)-5-methyl-pyrazole-4-COOCH₃ |
| CH₃ | CH₃ | 4-chloro-5-methyl-isothiazol-3-yl |
| CH₃ | C₃H₇ | 2,6-dimethyl-3-CON(CH₃)₂-pyridine |
| C₂H₅ | C₂H₅ | 3-methyl-2-COOCH₃-thiophene |
| CH₂—CH=CH₂ | C₂H₅ | 2-(COOCH₃)-benzyl— |
| CH₂—CH=CH₂ | CH₃ | 4-bromo-5-methyl-1-methyl-pyrazole |
| C₂H₅ | CH₃ | 2-(COOCH₃)-phenyl |
| C₂H₅ | C₂H₅ | 2-SO₂NCH₃(OCH₃)-phenyl |
| C₃H₇ | CH₂—CH=CH₂ | 2-CH₃-phenyl |

TABLE 1-continued

| Examples of the compounds of the formula (I) | | |
|---|---|---|
| R¹ | R² | R³ |
| CH₃ | CH₃ | 2-OCH₃-phenyl |
| cyclopropyl | C₂H₅ | 2-Cl-6-CH₃-phenyl |
| cyclopropyl | C₂H₅ | 2-Br-6-CH₃-phenyl |
| C₂H₅ | C₂H₅ | 4-Cl-5-methyl-1-methyl-pyrazol-3-yl |
| CH₃ | C₂H₅ | 2-(phenylsulfonyl)phenyl |
| CH₃ | C₃H₇ | 2-(OCHF₂)benzyl |
| C₃H₇ | CH₃ | 3-methyl-2-(COOCH₃)thiophene |
| C₃H₇ | CH₃ | 2-OCH₃-phenyl |
| C₃H₇ | C₂H₅ | 2-(OCH₂CH₂—Cl)phenyl |
| C₃H₇ | C₂H₅ | 2-F-phenyl |

TABLE 1-continued

Examples of the compounds of the formula (I)

| R¹ | R² | R³ |
|---|---|---|
| $CH_3$ | $C_2H_5$ | (phenyl attached to isoxazoline-type ring with C=N, O) |
| $CH_3$ | $CH_3$ | 2-methyl-3-trifluoromethyl-pyridinyl |
| $C_2H_5$ | $CH_3$ | naphthyl |
| $CH_3$ | $C_2H_5$ | 2-methyl-3-sulphamoyl-pyridinyl ($SO_2NH_2$) |
| $C_2H_5$ | $C_2H_5$ | 2-methyl-3-sulphamoyl-pyridinyl ($SO_2NH_2$) |
| cyclopropyl | $CH_3$ | 2-methyl-3-sulphamoyl-pyridinyl ($SO_2NH_2$) |
| $CH_3$ | $C_2H_5$ | 3-methyl-2-($OCF_2-CF_2Cl$)-thienyl |
| $C_2H_5$ | $CH_3$ | 2-methyl-(2-chloroethoxy)phenyl ($OCH_2CH_2-Cl$) |

If, for example, 2,6-difluoro-phenylsulphonyl isocyanate and 5-ethoxy-4-methoxy-2,4-dihydro-3H-1,2,4-triazol-3-one are used as starting substances, the course of the reaction in process (a) according to the invention can be outlined by the following equation:

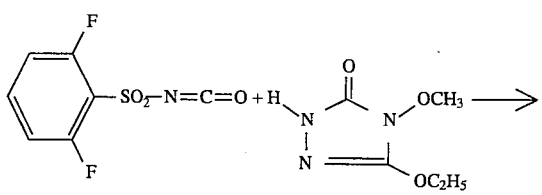

-continued

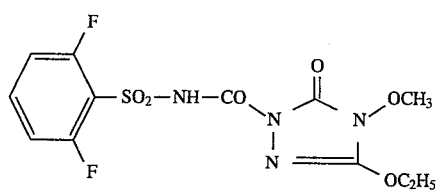

If, for example, 2-methylthio-benzenesulphonamide and 2-chlorocarbonyl-4-ethoxy-5-propyloxy-2,4-dihydro-3H-1,2,4-triazol-3-one are used as starting substances, the course of the reaction in process (b) according to the invention can be outlined by the following equation:

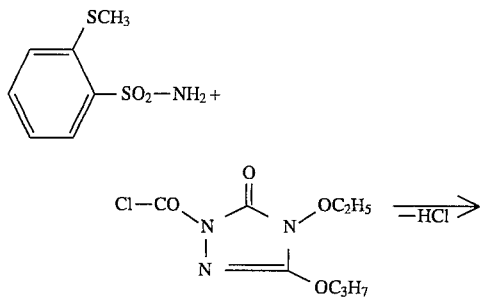

If, for example, N-methoxycarbonyl-2-methoxy-benzene-sulphonamide and 5-methoxy-4-difluoromethoxy-2,4-dihydro-3H-1,2,4-triazol-3-one are used as starting substances, the course of the reaction in process (c) according to the invention can be outlined by the following equation:

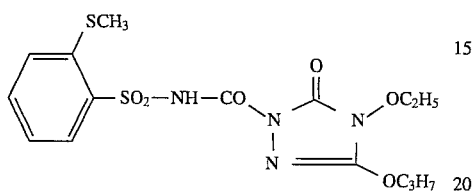

Formula (II) provides a general definition of the triazolinones to be used as starting substances in processes (a) and (c) according to the invention for the preparation of compounds of the formula (I).

In formula (II), $R^1$ and $R^2$ preferably, or in particular, have those meanings which have already been mentioned above in connection with the description of the compounds of the formula (I) according to the invention as being preferred, or particularly preferred, for $R^1$ and $R^2$.

Examples of the starting substances of the formula (II) are listed in Table 2 below.

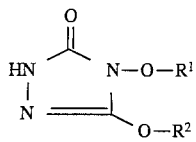

(II)

TABLE 2

Examples of the starting substances of the formula (II)

| $R^1$ | $R^2$ |
|---|---|
| H | $CH_3$ |
| $CH_3$ | $CH_3$ |
| $C_2H_5$ | $CH_3$ |
| $C_3H_7$ | $CH_3$ |
| $CH(CH_3)$ | $CH_3$ |
| $C_4$ | $CH_3$ |
| △ | △ |
| $CH_3$ | $C_2H_5$ |
| $CH_3$ | $C_3H_7$ |
| $CH_3$ | $CH(CH_3)_2$ |
| $CH_3$ | $CH_2-CH=CH_2$ |
| $CH_3$ | $CH_2$—〈phenyl〉 |
| $CH_3$ | $CH_2-C=CH$ |
| $C_2H_5$ | $C_2H_5$ |
| $C_3H_7$ | $C_2H_5$ |
| △ | $C_2H_5$ |
| $CH_2-CH=CH_2$ | $C_2H_5$ |
| △ | $C_3H_7$ |
| △ | $CH_2-CH=CH_2$ |
| $C_2H_5$ | $CH(CH_3)_2$ |
| $C_3H_7$ | $CH(CH_3)_2$ |
| $CH_2-CH=CH_2$ | $C_3H_7$ |
| $C_2H_5$ | $C_3H_7$ |
| $C_2H_5$ | $-CH_2-C\equiv CH$ |
| $C_3H_7$ | $C_3H_7$ |
| H | $C_2H_5$ |
| H | $C_3H_7$ |
| H | $CH(CH_3)_2$ |
| H | $-CH_2-CH=CH_2$ |
| H | $-CH_2-C\equiv CH$ |
| H | $-CH_2$—〈phenyl〉 |

With the exception of the compounds 4-hydroxy-5-methoxy- and 4-hydroxy-5-ethoxy-2,4-dihydro-3H-1,2,4-triazol-3-one [cf. Arch. Pharm. (Weinheim) Vol. 301, p. 827–829 (1968)], the starting substances of the formula (II) were hitherto unknown from the literature and are, as new substances, also a subject of the present patent application.

The compounds of the formula (II) are obtained when 4-hydroxy-semicarbazide, of the formula (VII), $$H_2N-NH-CO-NH-OH \qquad (VII)$$

is reacted with orthocarbonates of the general formula (VIII)

$$C(OR^2)_4 \qquad (VIII)$$

in which $R^2$ has the abovementioned meaning, if appropriate in the presence of a diluent such as, for example, methanol, ethanol or propanol, at temperatures between 0° C. and 150° C. and, if appropriate, the resulting compounds of the general formula (IIa)

in which

R² has the abovementioned meaning, are reacted with alkylating agents of the general formula (IX)

R¹—X     (IX)

in which

X represents chlorine, bromine, iodine, methylsulphonyloxy, trifluoromethylsulphonyloxy, phenylsulphonyloxy, tolylsulphonyloxy, or one of the groups —O—CO—OR¹ or —O—SO₂—OR¹ and R¹ has the abovementioned meaning with the exception of hydrogen, if appropriate in the presence of a diluent such as, for example, methanol, ethanol or propanol, and if appropriate in the presence of an acid binder such as, for example, sodium hydroxide, potassium carbonate or triethylamine, at temperatures between –30° C. and +100° C. (cf. the Preparation Examples).

Formula (III) provides a general definition of the sulphonyl isocyanates furthermore to be used as starting substances in process (a) according to the invention for the preparation of compounds of the formula (I).

In formula (III), R³ preferably, or in particular, has the meaning which has already been mentioned above in connection with the description of the compounds of the formula (I) according to the invention as being preferred, or particularly preferred, for R³.

Examples of the starting substances of the formula (III) which may be mentioned are: 2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl-phenylsulphonylisocyanate, 2-fluoro-, 2-chloro-, 2-difluoromethoxy-, 2-trifluoromethoxy-, 2-methoxycarbonyl- and 2-ethoxycarbonyl-benzylsulphonyl isocyanate, 2-methoxycarbonyl-3-thienylsulphonyl isocyanate, 4-methoxycarbonyl- and 4-ethoxycarbonyl-1-methyl-pyrazol-5-yl-sulphonyl isocyanate.

The sulphonyl isocyanates of the formula (III) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (a) according to the invention for the preparation of the new compounds of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

When carrying out process (a) according to the invention, the reaction temperatures can be varied within a substantial range. In general, the process is carried out at temperatures between 0° C. and 150° C., preferably at temperatures between 10° C. and 80° C.

Process (a) according to the invention is generally carried out under atmospheric pressure.

For carrying out process (a) according to the invention, between 1 and 3 moles, preferably between 1 and 2 moles, of sulphonyl isocyanate of the formula (III) is generally employed per mole of triazolinone of the formula (II).

The reactants can be combined in any desired sequence. The reaction mixture is stirred until the reaction is complete, and the product is isolated by filtration with suction. In another processing variant, the mixture is concentrated, and the crude product, which remains in the residue, is brought to crystallisation using a suitable solvent such as, for example, diethyl ether. The product of the formula (I), which is obtained in crystalline form in this process, is isolated by filtration with suction.

Formula (IV) provides a general definition of the triazolinone derivatives to be used as starting substances in process (b) according to the invention for the preparation of compounds of the formula (I).

In formula (IV), R¹ and R² preferably, or in particular, have the meanings which have already been mentioned above in connection with the description of the compounds of the formula (I) according to the invention as being preferred, or particularly preferred, for R¹ and R², and Z preferably represents chlorine, C₁–C₄-alkoxy, benzyloxy or phenoxy, in particular methoxy or phenoxy.

Examples of the starting substances of the formula (IV) which are possible are the compounds of the formula (IV) which are to be prepared with the compounds of the formula (II) which are listed in Table 2 and phosgene, methyl chloroformate, benzyl chloroformate, phenyl chloroformate or diphenyl carbonate.

The starting substances of the formula (IV) were hitherto unknown and, as new substances, also a subject of the present invention.

The new triazolinone derivatives of the formula (IV) are obtained when triazolinones of the general formula (II)

in which

R¹ and R² have the abovementioned meanings, are reacted with carbonic acid derivatives of the general formula (X)

Z—CO—Z¹     (X)

in which

Z has the abovementioned meaning and

Z¹ represents a leaving group such as chlorine, methoxy, benzyloxy or phenoxy, if appropriate in the presence of a diluent such as, for example, tetrahydrofuran, and if appropriate in the presence of an acid acceptor such as, for example, sodium hydride or potassium tert-butylate, at temperatures between −20° C. and +100° C.

Formula (V) provides a general definition of the sulphonamides furthermore to be used as starting substances in process (b) according to the invention for the preparation of compounds of the formula (I).

In formula (V), $R^3$ preferably, or in particular, has the meaning which has already been mentioned above in connection with the description of the compounds of the formula (I) according to the invention as being preferred, or particularly preferred, for $R^3$.

Examples of the starting substances of the formula (V) which may be mentioned are: 2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl, 2-ethoxycarbonyl-, 2-propoxycarbonyl- and 2-isopropoxycarbonyl-benzenesulphonamide, 2-fluoro-, 2-chloro-, 2-difluoromethoxy-, 2-trifluoromethoxy-, 2-methoxycarbonyl- and 2-ethoxycarbonyl-phenylmethanesulphonamide, 2-methoxycarbonyl-3-thiophenesulphonamide, 4-methoxycarbonyl- and 4-ethoxycarbonyl-1-methyl-pyrazole-5-sulphonamide.

The sulphonamides of the formula (V) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (b) according to the invention for the preparation of the new compounds of the formula (I) is preferably carried out using diluents. Diluents which are suitable for this purpose are all inert organic solvents, for example those which are indicated above in process (a) according to the invention.

Acid acceptors which can be employed in process (b) according to the invention.are all acid binders which can customarily be used for reactions of this type. The following are preferably suitable: alkali metal hydroxides such as, for example, sodium hydroxide and potassium hydroxide, alkaline earth metal hydroxides such as, for example, calcium hydroxide, alkali metal carbonates and alkali alcoholates and metal such as sodium carbonate potassium carbonate, sodium tert-butylate and potassium tert-butylate, further aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out process (b) according to the invention, the reaction temperatures can be varied within a substantial range. In general, the process is carried out at temperatures between 0° C. and 100° C., preferably at temperatures between 10° C. and 60° C.

Process (b) according to the invention is generally carried out under atmospheric pressure. However, it is also possible to carry out the process under increased or reduced pressure.

For carrying out process (b) according to the invention, the starting substances required in each case are generally employed in approximately equimolar amounts. However, it is also possible to use one of the two components employed in each case in a larger excess. The reactions are generally carried out in a suitable diluent in the presence of an acid acceptor, and the reaction mixture is stirred for several hours at the temperature required in each case. Working-up in process (b) according to the invention is carried out in each case by customary methods.

The triazolinones of the formula (II) which are to be used as starting substances in process (c) according to the invention for the preparation of compounds of the formula (I) have already been described as starting substances for process (a) according to the invention.

Formula (VI) provides a general definition of the sulphonamide derivatives furthermore to be used as starting substances in process (c) according to the invention for the preparation of compounds of the formula (I).

In formula (VI), $R^3$ and Z preferably, or in particular, have those meanings which have already been mentioned above in connection with the description of the compounds of the formula (I) and (IV), respectively, according to the invention as being preferred, or particularly preferred, for $R^3$ and Z.

Process (c) according to the invention is preferably carried out using diluents. Substances which are suitable for this purpose are the same organic solvents which have been mentioned above in connection with the description of process (a) according to the invention.

If appropriate, process (c) is carried out in the presence of an acid acceptor. Substances which are suitable for this purpose are the same acid binders which have been mentioned above in connection with the description of process (b) according to the invention.

When carrying out process (c) according to the invention, the reaction temperatures can be varied within a substantial range. In general, the process is carried out at temperatures between 0° C. and 100° C., preferably at temperatures between 10° C. and 60° C.

Process (c) according to the invention is generally carried out under atmospheric pressure. However, it is also possible to carry out the process under increased or reduced pressure.

For carrying out process (c) according to the invention, the starting substances required in each case are generally employed in approximately equimolar amounts. However, it is also possible to use one of the two components employed in each case in a larger excess. The reactions are generally carried out in a suitable diluent in the presence of an acid acceptor, and the reaction mixture is stirred for several hours at the temperature required in each case. Working-up in process (c) according to the invention is carried out in each case by customary methods.

To convert the compounds of the formula (I) into salts, they are stirred with suitable salt formers such as, for example, sodium hydroxide, sodium methylate or sodium ethylate or potassium hydroxide, potassium methylate or potassium ethylate, ammonia, isopropylamine, dibutylamine or triethylamine, in suitable diluents such as, for example, water, methanol or ethanol. The salts can be isolated in the form of crystalline products, if appropriate after concentration.

The active compounds according to the invention can be used as defoliants, desiccants, agents for destroying broad-leaved plants and, especially, as weed-killers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, CAmodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example. lignin-sulphite waste liquors and methylcellulose.

Adhesives such as carboxymethylcellulose and natural and synthetic polymers in the form of powders, granules or latexes, such as gum arabic, polArvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoates such as, for example, diclofop-methyl, fenoxapropethyl, fluazifopbutyl, haloxyfop-methyl and quizalofopethyl; azinones such as, for example, chloridazon and norflurazon; carbamates such as, for example, chlorpropham, desmedipham, phenmediphamand propham; chloroacetanilides such as, for example, alachlor, acetochlor, butachlor, metazachlor, metolachlor, pretilachlor and propachlor; dinitroanilines such as, for example, oryzalin, pendimethalin and trifluraiin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribehuron-methyl; thiocarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazol, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

Preparation Examples

Example 1

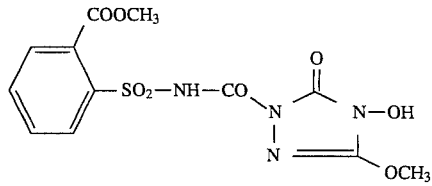

(Process (a))

A mixture of 1.31 g (10 mmol) of 4-hydroxy-5-methoxy-2,4-dihydro-3H-1,2,4-triazol-3-one, 2.89 g (12 mmol) of 2-methoxycarbonyl-phenylsulphonyl isocyanate and 40 ml of acetonitrile is stirred for 5 hours at 20° C. and subsequently concentrated under a water pump vacuum. The residue is stirred with diethyl ether, and the product which has been obtained in crystalline form is isolated by filtration with suction and recrystallised from isopropanol. 1.22 g (33% of theory) of 4-hydroxy-5-methoxy-1-(2-methoxycarbonyl-phenylsulphonylaminocarbonyl)-2,4-dihydro-3H-1,2,4-triazol-3-one of melting point 180° C. are obtained.

Other compounds of the formula (I) which can be prepared analogously to Example 1 and following the general description of the preparation processes according to the invention are, for example, those listed in Table 3 below.

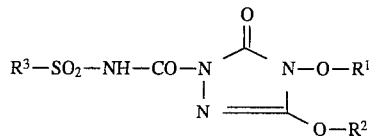

TABLE 3

Preparation examples of the compounds of the formula (I)

| Ex. No. | $R^1$ | $R^2$ | $R^3$ | Melting point (°C.) |
|---|---|---|---|---|
| 2 | $CH_3$ | $CH_3$ | 2-$CO_2CH_3$-phenyl | 119 |
| 3 | $CH_3$ | $CH_3$ | 2-Cl-phenyl | 111 |
| 4 | $CH_3$ | $CH_3$ | 2-$OCF_3$-phenyl | 109 |
| 5 | $CH_3$ | $CH_3$ | 2-Cl-6-$CH_3$-phenyl | 126 |
| 6 | H | $CH_3$ | 2-Cl-phenyl | 169 |
| 7 | H | $CH_3$ | 2-$OCF_3$-phenyl | 161 |
| 8 | H | $CH_3$ | 2-Cl-6-$CH_3$-phenyl | 119 |
| 9 | $CH_3$ | $CH_3$ | 2-$OCHF_2$-phenyl | 151 |
| 10 | $CH_3$ | $C_2H_5$ | 2-$CO_2CH_3$-phenyl | 127 |
| 11 | $CH_3$ | $CH_3$ | 2-F-phenyl | 158 |

TABLE 3-continued

Preparation examples of the compounds of the formula (I)

| Ex. No. | R$^1$ | R$^2$ | R$^3$ | Melting point (°C.) |
|---|---|---|---|---|
| 12 | CH$_3$ | CH$_3$ | 2-CF$_3$-phenyl | 124 |
| 13 | CH$_3$ | CH$_3$ | 2-CH$_3$-phenyl | 71 |
| 14 | CH$_3$ | C$_2$H$_5$ | 2-Cl-phenyl | 90 |
| 15 | CH$_3$ | C$_2$H$_5$ | 2-Cl-3-CH$_3$-phenyl | 91 |
| 16 | CH$_3$ | C$_2$H$_5$ | 2-OCF$_3$-phenyl | 109 |
| 17 | CH$_3$ | C$_2$H$_5$ | 2-OCHF$_2$-phenyl | 98 |
| 18 | CH$_3$ | C$_2$H$_5$ | 2-CF$_3$-phenyl | 112 |
| 19 | CH$_3$ | C$_2$H$_5$ | 2-F-phenyl | 124 |
| 20 | CH$_3$ | C$_2$H$_5$ | 2-CH$_3$-phenyl | 87 |
| 21 | CH$_3$ | CH$_3$ | 2,6-di-Cl-phenyl | 170 |
| 22 | CH$_3$ | C$_2$H$_5$ | 2,6-di-Cl-phenyl | 119 |
| 23 | CH$_3$ | C$_2$H$_5$ | 3-methyl-2-(CO$_2$CH$_3$)-thienyl | 115 |
| 24 | CH$_3$ | C$_2$H$_5$ | 2,6-di-Cl-benzyl (CH$_2$-) | 104 |
| 25 | CH$_3$ | C$_2$H$_5$ | 2-CO$_2$C$_2$H$_5$-phenyl | 115 |
| 26 | H | CH$_3$ | 2-F-phenyl | 189 |
| 27 | H | CH$_3$ | 2-CH$_3$-phenyl | 171 |
| 28 | H | CH$_3$ | 2,6-di-Cl-phenyl | 192 |
| 29 | H | CH$_3$ | 2-CO$_2$C$_2$H$_5$-phenyl | 162 |

TABLE 3-continued

Preparation examples of the compounds of the formula (I)

| Ex. No. | R¹ | R² | R³ | Melting point (°C.) |
|---|---|---|---|---|
| 30 | H | $CH_3$ | 2-$CF_3$-phenyl 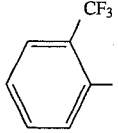 | 160 |
| 31 | $CH_3$ | $CH_3$ | 2-$CO_2C_2H_5$-phenyl 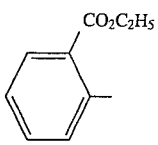 | 150 |
| 32 | $CH_3$ | $CH_3$ | 2-$CO_2C_3H_7$-phenyl 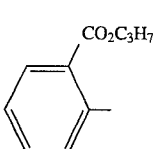 | 98 |
| 33 | $CH_3$ | $CH_3$ | 2,6-di-Cl-benzyl 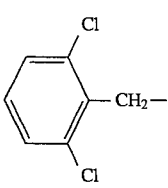 | 157 |
| 34 | $CH_3$ | $CH_3$ | 2-$OCF_3$-benzyl 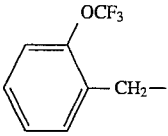 | 139 |
| 35 | $CH_3$ | $CH_3$ | 3-methyl-2-$CO_2CH_3$-thienyl 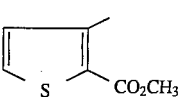 | 156 |
| 36 | $CH_3$ | $CH_3$ | 4-$CO_2C_2H_5$-5-methyl-1-methyl-pyrazolyl 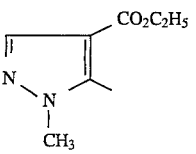 | 121 |
| 37 | H | $CH_3$ | 4-$CO_2C_2H_5$-5-methyl-1-methyl-pyrazolyl 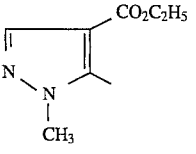 | 163 |
| 38 | H | $CH_3$ | 2-$OCF_3$-benzyl 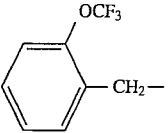 | 164 |
| 39 | H | $CH_3$ | 2-$OCHF_2$-phenyl 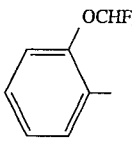 | 158 |

TABLE 3-continued

Preparation examples of the compounds of the formula (I)

| Ex. No. | R¹ | R² | R³ | Melting point (°C.) |
|---|---|---|---|---|
| 40 | $CH_3$ | $CH_3$ | 2-Br-phenyl 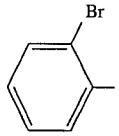 | 171 |
| 41 | H | $CH_3$ | 2-Br-phenyl 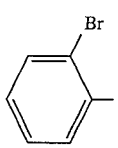 | 149 |
| 42 | H | $C_2H_5$ | 2-$CO_2CH_3$-phenyl 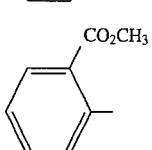 | 74 |
| 43 | H | $C_2H_5$ | 2-$CH_3$-phenyl 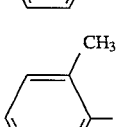 | 168 |
| 44 | H | $C_2H_5$ | 2-$CF_3$-phenyl 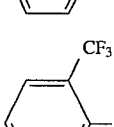 | 76 |
| 45 | H | $C_2H_5$ | 2-$OCF_3$-phenyl 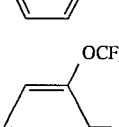 | 97 |
| 46 | $CH_3$ | $C_2H_5$ | 2-$OCF_3$-benzyl 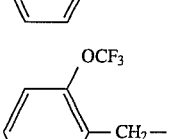 | 118 |
| 47 | $CH_3$ | $CH_3$ | 4-Br-3-methyl-1-methyl-pyrazolyl 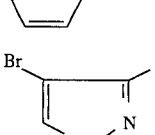 | 124 |
| 48 | $C_2H_5$ | $CH_3$ | 2-$COOCH_3$-phenyl 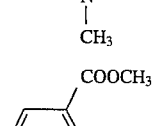 | 106 |

TABLE 3-continued

Preparation examples of the compounds of the formula (I)

| Ex. No. | R¹ | R² | R³ | Melting point (°C.) |
|---|---|---|---|---|
| 49 | $C_2H_5$ | $CH_3$ | 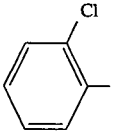 2-Cl-phenyl | 122 |
| 50 | $C_2H_5$ | $CH_3$ | 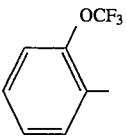 2-OCF₃-phenyl | 113 |
| 51 | $C_2H_5$ | $CH_3$ | 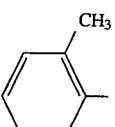 2-CH₃-phenyl | 141 |
| 52 | $C_2H_5$ | $CH_3$ | 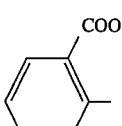 2-COOC₃H₇-n-phenyl | 88 |
| 53 | $C_2H_5$ | $CH_3$ | 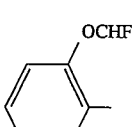 2-OCHF₂-phenyl | 118 |
| 54 | $C_2H_5$ | $CH_3$ | 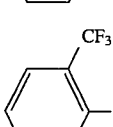 2-CF₃-phenyl | 119 |
| 55 | $C_2H_5$ | $CH_3$ | 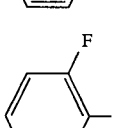 2-F-phenyl | 153 |
| 56 | $C_2H_5$ | $CH_3$ | 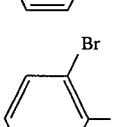 2-Br-phenyl | 128 |
| 57 | $C_2H_5$ | $CH_3$ | 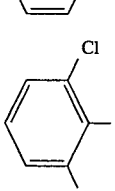 2,6-Cl₂-benzyl | 113 |
| 58 | $C_2H_5$ | $CH_3$ | 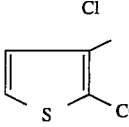 3-COOCH₃-thien-2-yl | 126 |
| 59 | $C_2H_5$ | $CH_3$ | 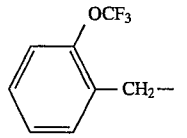 2-OCF₃-benzyl | 57 |
| 60 | $C_2H_5$ | $CH_3$ | 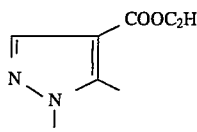 4-COOC₂H₅-1,5-dimethylpyrazol-3-yl | 144 |
| 61 | $CH_3$ | $C_2H_5$ | 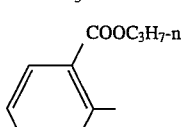 2-COOC₃H₇-n-phenyl | 101 |
| 62 | $CH_3$ | $C_2H_5$ | 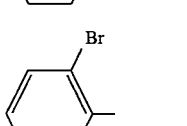 2-Br-phenyl | 87 |
| 63 | $CH_3$ | $C_2H_5$ | 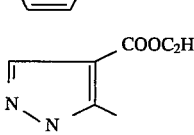 4-COOC₂H₅-1,5-dimethylpyrazol-3-yl | 63 |
| 64 | $C_2H_5$ | $CH_3$ | 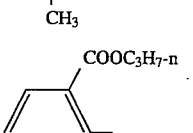 2-COOC₃H₇-n-phenyl | 125ˣ⁾ |
| 65 | $C_2H_5$ | $CH_3$ | 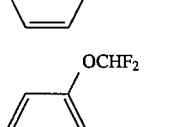 2-OCHF₂-phenyl | 105ˣ⁾ |
| 66 | $C_2H_5$ | $CH_3$ | 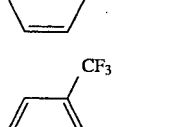 2-CF₃-phenyl | 132ˣ⁾ |
| 67 | $C_2H_5$ | $CH_3$ | 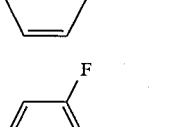 3-F-phenyl | 168ˣ⁾ |
| 68 | $C_2H_5$ | $CH_3$ | 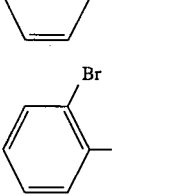 2-Br-phenyl | 85ˣ⁾ |

TABLE 3-continued

Preparation examples of the compounds of the formula (I)

| Ex. No. | $R^1$ | $R^2$ | $R^3$ | Melting point (°C.) |
|---|---|---|---|---|
| 69 | $CH_3$ | $CH_3$ | 2-$COOC_2H_5$-phenyl | 126[x)] |
| 70 | $CH_3$ | $C_2H_5$ | 2-$COOCH_3$-phenyl | 62[x)] |
| 71 | $CH_3$ | $C_2H_5$ | 2-$COOC_2H_5$-phenyl | 72[x)] |
| 72 | $CH_3$ | $C_2H_5$ | 2-$CF_3$-phenyl | 90[x)] |
| 73 | $CH_3$ | $C_2H_5$ | 2-$OCHF_2$-phenyl | 92[x)] |
| 74 | $CH_3$ | $CH_3$ | 2-$COOCH_3$-phenyl | 167[x)] |
| 75 | $CH_3$ | $CH_3$ | 2-$OCF_3$-phenyl | 112[x)] |
| 76 | $CH_3$ | $CH_3$ | 2-Cl-4-$CH_3$-phenyl | 75[x)] |
| 77 | $CH_3$ | $CH_3$ | 2-$CF_3$-phenyl | 94[x)] |
| 78 | $CH_3$ | $C_2H_5$ | 2-$OCF_3$-phenyl | 110[x)] |
| 79 | $CH_3$ | $CH_3$ | 2,4-di-$OCH_3$-phenyl | 131 |
| 80 | $CH_3$ | $CH_3$ | 2-$OCH_3$-phenyl | 114 |
| 81 | $CH_3$ | $CH_3$ | 2-$OC_2H_5$-phenyl | 148 |
| 82 | $C_2H_5$ | $CH_3$ | 2-$COOC_2H_5$-phenyl | 121 |
| 83 | $C_2H_5$ | $CH_3$ | 2,6-di-Cl-phenyl | 159 |
| 84 | $C_2H_5$ | $CH_3$ | 2-$SC_2H_5$-phenyl | 146 |
| 85 | $C_2H_5$ | $CH_3$ | 2-$COOC_2H_5$-phenyl | 61[x)] |
| 86 | $C_2H_5$ | $CH_3$ | 2,6-di-Cl-phenyl | 66[x)] |
| 87 | $C_2H_5$ | $CH_3$ | 2-$SC_2H_5$-phenyl | 54[x)] |

TABLE 3-continued

Preparation examples of the compounds of the formula (I)

| Ex. No. | R¹ | R² | R³ | Melting point (°C.) |
|---|---|---|---|---|
| 88 | $CH_3$ | $CH_3$ | 2-($S-CH_3$)phenyl | 110 |
| 89 | $CH_3$ | $CH_3$ | 2-($SC_2H_5$)phenyl | 119 |
| 90 | $CH_3$ | $CH_3$ | 2-($SO-C_2H_5$)phenyl | 157 |
| 91 | $CH_3$ | $CH_3$ | 2-($SO_2-C_2H_5$)phenyl | 204 |
| 92 | $CH_3$ | $CH_3$ | 2-($SO-CH_3$)phenyl | 130 |
| 93 | $CH_3$ | $CH_3$ | 2-($SO_2-CH_3$)phenyl | 169 |
| 94 | $CH_3$ | $CH_3$ | 2-($COOCH_3$)benzyl | 123 |
| 95 | $CH_3$ | $CH_3$ | 2-($OCHF_2$)benzyl | 96 |
| 96 | $C_2H_5$ | $C_2H_5$ | 2-($COOCH_3$)phenyl | 151 |
| 97 | $C_2H_5$ | $C_2H_5$ | 2-($CF_3$)phenyl | 134 |
| 98 | $C_2H_5$ | $C_2H_5$ | 2,4-di($OCH_3$)phenyl | 120 | x) isolated in the form of the Na-salt.

Starting substances of the formula (II)

Example (II-1)

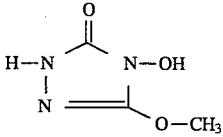

A mixture of 42 g (0.46 mol) of 4-hydroxysemicarbazide [R. Ohme, H. Preuschhof, J. Prakt. Chem. 313, (1971), p. 626], 73.3 g (0.54 mol) of tetramethyl orthocarbonate and 300 ml of methanol is refluxed for 18 hours. When the reaction mixture is cool, 250 ml of the solvent employed are distilled off under a water pump vacuum. The colourless product, which is obtained in the residue in crystalline form, is isolated by filtration with suction.

22 g (36% of theory) of 4-hydroxy-5-methoxy-2,4-dihydro-3H-1,2,4-triazol-3-one of melting point 211° C. (exothermal decomposition) are obtained; [cf. Arch. Pharm. Vol. 301, p. 829 (1968)].

Example (II-2)

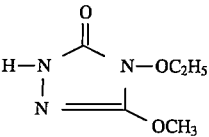

3.7 g (28 mmol) of 4-hydroxy-5-methoxy-2,4-dihydro-3H-1,2,4-triazol-3-one are suspended in 30 ml of ethanol, and the suspension is treated with 1.12 g (28 mmol) of sodium hydroxide, dissolved in 5 ml of water. After stirring has been continued for 2 hours at room temperature (20° C.), 4.3 g (28 mmol) of diethyl sulphate are added, and the mixture is stirred for a further 18 hours at room temperature. The reaction mixture is acidified with dilute hydrochloric acid (pH=3–4), filtered and concentrated under a water pump vacuum. The residue is stirred with 50 ml of methanol/diethyl ether (1:4), and the insoluble constituents are removed by filtration. The crude product, which is obtained by concentrating the filtrate, is purified by recrystallisation from isopropanol.

1.8 g (40% of theory) of 4-ethoxy-5-methoxy-2,4-dihydro-3H-1,2,4-triazol-3-one are obtained as a colourless solid of melting point 57° C.

Other compounds of the formula (II) which can be prepared analogously to Examples (II-1) and (II-2) are, for example, those listed in Table 4 below.

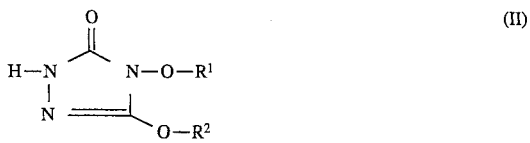

TABLE 4

| Examples of the starting substances of the formula (II) | | | |
|---|---|---|---|
| Ex. | $R^1$ | $R^2$ | Melting No. point (°C.) |
| II-3 | $CH_3$ | $CH_3$ | 147 |
| II-4 | H | $C_2H_5$ | 145 |
| II-5 | $CH_3$ | $C_2H_5$ | 118 |

Use Examples

In the use Examples, the following compound (A) is used as comparison substance:

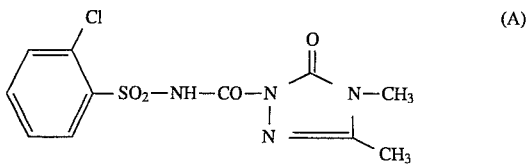

2-(2-Chloro-phenylsulphonylaminocarbonyl)-4,5-dimethyl-2,4-dihydro-3H-1,2,4-triazol-3-one (disclosed in EP-A 341,489).

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0%=no action (like untreated control)

100%=total destruction

A clearly superior activity compared with the prior art is shown, in this test, for example by the compounds of the following Preparation Examples: 5, 12 and 13.

Example 1

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

A clearly superior activity compared with the prior art is shown, in this test, for example by the compounds of the following Preparation Examples: 2, 4 and 20.

It will be appreciated that the instant specification and claims are set forth by way of illustration and not limitation, and that various modifications and changes may be made without departing from the spirit and scope of the present invention.

We claim:

1. A triazolinone of the formula

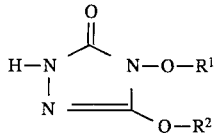

in which $R^1$ represents $C_1$–$C_6$-alkyl, $C_1$–$C_6$-alkyl substituted by one or more members selected from the group consisting of fluorine, chlorine, bromine, cyano, $C_1$–$C_4$-alkoxy, $C_1$–$C_4$-alkylcarbonyl and $C_1$–$C_4$-alkoxycarbonyl, or represents $C_3$–$C_6$-alkenyl or $C_3$–$C_6$-alkinyl, or represents $C_3$–$C_6$-alkenyl or $C_3$–$C_6$-alkinyl each of which is substituted by one or more members selected from the group consisting of fluorine, chlorine and bromine, or represents $C_3$–$C_7$-cycloalkyl or $C_4$–$C_7$-cycloalkenyl, or represents $C_3$–$C_7$-cycloalkyl or $C_4$–$C_7$-cycloalkenyl each of which is substituted by one or more members selected from the group consisting of fluorine, chlorine, bromine and $C_1$–$C_4$-alkyl, or represents phenyl-$C_1$–$C_3$-alkyl, or phenyl $C_1$–$C_3$-alkyl which is substituted by one or more members selected from the group consisting of fluorine, chlorine, bromine, cyano, nitro, $C_1$–$C_4$-alkyl, trifluoromethyl, $C_1$–$C_4$-alkoxy and $C_1$–$C_4$-alkoxy-carbonyl, and $R^2$ represents $C_1$–$C_6$-alkyl or $C_1$–$C_6$-alkyl which is substituted by one or more members selected from the group consisting of fluorine, chlorine, bromine, cyano, $C_3$–$C_6$-cycloalkyl, $C_1$–$C_4$alkoxy and $C_1$–$C_4$-alkoxycarbonyl, or represents $C_3$–$C_6$-alkenyl or $C_3$–$C_6$-alkinyl, or represents $C_3$–$C_6$-alkenyl or $C_3$–$C_6$-alkinyl each of which is substituted by one or more selected from the group consisting of fluorine, chlorine, and bromine, or represents $C_3$–$C_6$-cycloalkyl, or $C_3$–$C_6$-cycloalkyl which is substituted by one or more members selected from the group consisting of fluorine, chlorine, bromine and $C_1$–$C_4$-alkyl, or represents cyclohexenyl, or represents phenyl-$C_1$–$C_3$-alkyl, or phenyl-$C_1$–$C_3$-alkyl which is substituted by one or more members selected from the group consisting of fluorine, chlorine, bromine, cyano, nitro, $C_1$–$C_4$-alkyl, trifluoromethyl, $C_1$–$C_4$-alkoxy and $C_1$–$C_4$-alkoxy-carbonyl.

2. A triazolinone according to claim 1 in which $R^1$ represents $C_1$–$C_4$-alkyl, $C_1$–$C_4$-alkyl which is substituted by one or more members selected from the group consisting of fluorine, cyano, methoxy and ethoxy, or represents allyl, or represents $C_3$–$C_6$-cycloalkyl, or represents benzyl, and $R^2$ represents $C_1$–$C_4$-alkyl, or $C_1$–$C_4$-alkyl which is substituted by one or more members selected from the group consisting of fluorine, chlorine, methoxy and ethoxy, or represents $C_3$–$C_4$-alkenyl, or $C_3$–$C_4$-alkenyl which is substituted by one or more members selected from the group consisting of fluorine and chlorine, or represents $C_3$–$C_6$-cycloalkyl, or represents benzyl, or benzyl which is substituted by one or more selected from the group consisting of fluorine, chlorine and methyl.

3. A compound according to claim 1, which has the formula

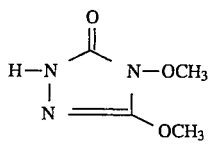

4. A compound according to claim 1, which has the formula

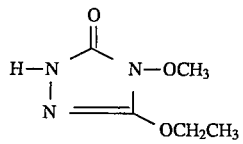

5. A compound according to claim 1, which has the formula

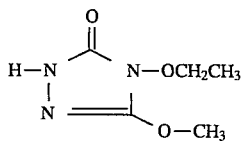

6. A compound according to claim 1, which has the formula

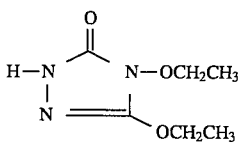

* * * * *

UNITED STATES PATENT AND TRADEMARK OFFICE
CERTIFICATE OF CORRECTION

PATENT NO. : 5,554,761
DATED : September 10, 1996
INVENTOR(S) : Haas, et al.

It is certified that error appears in the above-indentified patent and that said Letters Patent is hereby corrected as shown below:

Col. 42, line 64    After " more " insert -- members --

Signed and Sealed this

Eighteenth Day of March, 1997

Attest:

BRUCE LEHMAN

*Attesting Officer*        Commissioner of Patents and Trademarks